(12) United States Patent
Casey et al.

(10) Patent No.: US 11,432,943 B2
(45) Date of Patent: Sep. 6, 2022

(54) SYSTEMS AND METHODS FOR ORTHOPEDIC IMPLANT FIXATION

(71) Applicant: CARLSMED, INC., Carlsbad, CA (US)

(72) Inventors: Niall Patrick Casey, Carlsbad, CA (US); Michael J. Cordonnier, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 35 days.

(21) Appl. No.: 16/352,699

(22) Filed: Mar. 13, 2019

(65) Prior Publication Data
US 2019/0282367 A1    Sep. 19, 2019

Related U.S. Application Data

(60) Provisional application No. 62/643,046, filed on Mar. 14, 2018.

(51) Int. Cl.
*A61F 2/44* (2006.01)
*A61F 2/30* (2006.01)

(52) U.S. Cl.
CPC .......... *A61F 2/447* (2013.01); *A61F 2/30749* (2013.01); *A61F 2/442* (2013.01); *A61F 2/446* (2013.01); *A61F 2/4455* (2013.01); *A61F 2/4465* (2013.01); *A61F 2002/3079* (2013.01); *A61F 2002/30115* (2013.01); *A61F 2002/30125* (2013.01); *A61F 2002/30131* (2013.01); *A61F 2002/30143* (2013.01); *A61F 2002/30146* (2013.01); *A61F 2002/30166* (2013.01); *A61F 2002/30261* (2013.01);
(Continued)

(58) Field of Classification Search
None
See application file for complete search history.

(56) References Cited

U.S. PATENT DOCUMENTS

| 4,704,686 A | 11/1987 | Aldinger |
| 4,936,862 A | 6/1990 | Walker et al. |

(Continued)

FOREIGN PATENT DOCUMENTS

| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION satire series clinical application." Medical Now, No. 78; Aug. 2015, 4 pages.

(Continued)

*Primary Examiner* — Julianna N Harvey
(74) *Attorney, Agent, or Firm* — Perkins Coie LLP (57) ABSTRACT

An interbody implant system for use in the spine includes a base comprising two or more bone contacting surfaces, at least one recess in at least one of the two or more bone contacting surfaces, the recess configured for containing a tooth, a deployable tooth to provide fixation between the base and the anatomy of a subject, a break-away bridge between the tooth and the base for providing a first relative position between the tooth and the base, and a locking mechanism for providing a second relative position between the tooth and the base.

17 Claims, 8 Drawing Sheets

(52) U.S. Cl.
CPC .............. *A61F 2002/30579* (2013.01); *A61F 2002/30593* (2013.01); *A61F 2002/30784* (2013.01)

(56) References Cited

U.S. PATENT DOCUMENTS

| | | | |
|---|---|---|---|
| 5,431,562 A | 7/1995 | Andreiko et al. | |
| 6,696,073 B2 * | 2/2004 | Boyce | A61F 2/32 |
| | | | 424/422 |
| 6,772,026 B2 | 8/2004 | Bradbury | |
| 6,932,842 B1 | 8/2005 | Litschko et al. | |
| 6,978,188 B1 | 12/2005 | Christensen | |
| 6,988,241 B1 | 1/2006 | Guttman | |
| 7,174,282 B2 | 2/2007 | Hollister et al. | |
| 7,187,790 B2 | 3/2007 | Sabol et al. | |
| D548,242 S | 8/2007 | Viegers | |
| 7,747,305 B2 | 6/2010 | Dean et al. | |
| 7,756,314 B2 | 7/2010 | Karau et al. | |
| 7,799,077 B2 | 9/2010 | Lang | |
| 8,246,680 B2 | 8/2012 | Betz | |
| 8,265,949 B2 | 9/2012 | Haddad | |
| 8,275,594 B2 | 9/2012 | Lin | |
| 8,337,507 B2 | 12/2012 | Lang | |
| 8,394,142 B2 | 3/2013 | Bertagnoli | |
| 8,457,930 B2 | 6/2013 | Shroeder | |
| 8,532,806 B1 | 9/2013 | Masson | |
| 8,556,983 B2 | 10/2013 | Bojarski et al. | |
| 8,644,568 B1 | 2/2014 | Hoffman | |
| 8,735,773 B2 | 5/2014 | Lang | |
| 8,758,357 B2 | 6/2014 | Frey | |
| 8,775,133 B2 | 7/2014 | Schroeder | |
| 8,781,557 B2 | 7/2014 | Dean | |
| 8,843,229 B2 | 9/2014 | Vanasse | |
| 8,855,389 B1 | 10/2014 | Hoffman | |
| 8,870,889 B2 | 10/2014 | Frey | |
| 9,020,788 B2 | 4/2015 | Lang | |
| 9,198,678 B2 | 12/2015 | Frey et al. | |
| 9,208,558 B2 | 12/2015 | Dean | |
| D761,842 S | 7/2016 | Johnson | |
| 9,411,939 B2 | 8/2016 | Furrer | |
| 9,445,907 B2 | 9/2016 | Ridew | |
| 9,452,050 B2 | 9/2016 | Miles et al. | |
| 9,542,525 B2 | 1/2017 | Arisoy et al. | |
| 9,642,633 B2 | 5/2017 | Frey et al. | |
| 9,693,831 B2 | 7/2017 | Mosnier et al. | |
| 9,707,058 B2 | 7/2017 | Bassett | |
| 9,715,563 B1 | 7/2017 | Schroeder | |
| 9,757,245 B2 | 9/2017 | O'Neil et al. | |
| 9,775,680 B2 | 10/2017 | Bojarski et al. | |
| 9,782,228 B2 | 10/2017 | Mosnier et al. | |
| 9,993,341 B2 | 6/2018 | Vanasse | |
| 10,034,676 B2 | 7/2018 | Donner | |
| 10,089,413 B2 | 10/2018 | Wirx-Speetjens et al. | |
| D841,675 S | 2/2019 | Hoffman | |
| 10,213,311 B2 | 2/2019 | Mafhouz | |
| D845,973 S | 4/2019 | Jaycobs | |
| D845,974 S | 4/2019 | Cooperman | |
| D847,165 S | 4/2019 | Kolbenheyer | |
| D848,468 S | 5/2019 | Ng | |
| D849,029 S | 5/2019 | Cooperman | |
| D849,773 S | 5/2019 | Jiang | |
| 10,292,770 B2 | 5/2019 | Ryan | |
| 10,299,863 B2 | 5/2019 | Grbic et al. | |
| 10,390,958 B2 | 8/2019 | Maclennan | |
| D860,237 S | 9/2019 | Li | |
| D860,238 S | 9/2019 | Bhardwaj | |
| D867,379 S | 11/2019 | Ang | |
| D867,389 S | 11/2019 | Jamison | |
| 10,463,433 B2 | 11/2019 | Turner et al. | |
| D870,762 S | 12/2019 | Mendoza | |
| 10,512,546 B2 | 12/2019 | Kamer et al. | |
| 10,517,681 B2 | 12/2019 | Roh et al. | |
| D872,117 S | 1/2020 | Kobayashi | |
| D872,756 S | 1/2020 | Howell | |
| D874,490 S | 2/2020 | Dodsworth | |
| D875,761 S | 2/2020 | Heffernan | |
| D876,454 S | 2/2020 | Knowles | |
| D877,167 S | 3/2020 | Knowles | |
| D879,112 S | 3/2020 | Hejazi | |
| 10,588,589 B2 | 3/2020 | Bregman-Amitai et al. | |
| 10,603,055 B2 | 3/2020 | Donner et al. | |
| D880,513 S | 4/2020 | Wang | |
| D881,908 S | 4/2020 | Sunil | |
| D881,910 S | 4/2020 | Lin | |
| 10,621,289 B2 | 4/2020 | Schroeder | |
| 10,631,988 B2 | 4/2020 | Arnold et al. | |
| 10,646,236 B2 | 5/2020 | Donner et al. | |
| 10,646,258 B2 | 5/2020 | Donner et al. | |
| 10,736,698 B2 | 8/2020 | Bohl | |
| 10,751,188 B2 | 8/2020 | Guo et al. | |
| 10,806,597 B2 | 10/2020 | Sournac et al. | |
| 10,902,944 B1 | 1/2021 | Casey et al. | |
| 11,000,334 B1 | 5/2021 | Young | |
| 2002/0007294 A1 | 1/2002 | Bradbury et al. | |
| 2004/0171924 A1 | 9/2004 | Mire et al. | |
| 2005/0049590 A1 * | 3/2005 | Alleyne | A61F 2/442 |
| | | | 623/17.11 |
| 2005/0271996 A1 | 12/2005 | Sporbert et al. | |
| 2006/0009780 A1 | 1/2006 | Foley | |
| 2007/0118243 A1 | 5/2007 | Schroeder | |
| 2007/0276501 A1 | 11/2007 | Betz | |
| 2008/0161680 A1 | 7/2008 | von Jako | |
| 2008/0195240 A1 | 8/2008 | Martin | |
| 2010/0191088 A1 | 7/2010 | Anderson | |
| 2010/0292963 A1 | 11/2010 | Schroeder | |
| 2011/0218545 A1 | 9/2011 | Catanzarite et al. | |
| 2011/0301710 A1 | 12/2011 | Mather et al. | |
| 2012/0010710 A1 | 1/2012 | Frigg | |
| 2012/0084064 A1 | 4/2012 | Dzenis et al. | |
| 2012/0116203 A1 | 5/2012 | Vancraen | |
| 2012/0150243 A9 | 6/2012 | Crawford | |
| 2012/0191192 A1 | 7/2012 | Park | |
| 2012/0287238 A1 | 11/2012 | Onishi | |
| 2012/0296433 A1 | 11/2012 | Farin | |
| 2013/0211531 A1 | 8/2013 | Steines et al. | |
| 2014/0072608 A1 | 3/2014 | Karagkiozaki | |
| 2014/0074438 A1 | 3/2014 | Furrer | |
| 2014/0081659 A1 | 3/2014 | Nawana et al. | |
| 2014/0086780 A1 | 3/2014 | Miller | |
| 2014/0164022 A1 | 6/2014 | Reed | |
| 2014/0350614 A1 | 11/2014 | Frey | |
| 2015/0105891 A1 | 4/2015 | Golway et al. | |
| 2015/0305878 A1 * | 10/2015 | O'Neil | A61B 8/12 |
| | | | 623/17.16 |
| 2015/0324490 A1 | 11/2015 | Page | |
| 2015/0328004 A1 | 11/2015 | Mafhouz | |
| 2016/0015465 A1 | 1/2016 | Steines et al. | |
| 2016/0074048 A1 | 3/2016 | Pavlovskaia | |
| 2016/0117817 A1 | 4/2016 | Seel | |
| 2016/0143744 A1 | 5/2016 | Bojarski et al. | |
| 2016/0210374 A1 | 7/2016 | Mosnier et al. | |
| 2016/0217268 A1 | 7/2016 | Otto | |
| 2016/0242857 A1 | 8/2016 | Scholl | |
| 2016/0300026 A1 | 10/2016 | Bogoni et al. | |
| 2016/0354039 A1 | 12/2016 | Soto et al. | |
| 2016/0378919 A1 | 12/2016 | McNutt et al. | |
| 2017/0000566 A1 | 1/2017 | Gordon | |
| 2017/0014169 A1 | 1/2017 | Dean | |
| 2017/0035514 A1 | 2/2017 | Fox et al. | |
| 2017/0061375 A1 | 3/2017 | Laster | |
| 2017/0068792 A1 | 3/2017 | Reiner | |
| 2017/0135706 A1 | 5/2017 | Frey et al. | |
| 2017/0143494 A1 | 5/2017 | Mahfouz | |
| 2017/0143831 A1 | 5/2017 | Varanasi et al. | |
| 2017/0216047 A1 | 8/2017 | Hawkes et al. | |
| 2017/0220740 A1 | 8/2017 | D'Urso | |
| 2017/0252107 A1 | 9/2017 | Turner et al. | |
| 2017/0262595 A1 | 9/2017 | Vorhis | |
| 2017/0367645 A1 | 12/2017 | Klinder | |
| 2018/0008349 A1 | 1/2018 | Gillman | |
| 2018/0116727 A1 | 5/2018 | Caldwell et al. | |
| 2018/0168499 A1 | 6/2018 | Bergold | |
| 2018/0168731 A1 | 6/2018 | Reid | |
| 2018/0185075 A1 | 7/2018 | She | |

(56) References Cited

U.S. PATENT DOCUMENTS

| | | |
|---|---|---|
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0338841 A1* | 11/2018 | Miller .................... A61B 17/80 |
| 2019/0029757 A1 | 1/2019 | Roh et al. |
| 2019/0146458 A1 | 5/2019 | Roh et al. |
| 2019/0167435 A1 | 6/2019 | Cordonnier |
| 2019/0201106 A1 | 7/2019 | Siemionow |
| 2019/0262084 A1 | 8/2019 | Roh et al. |
| 2019/0321193 A1 | 10/2019 | Casey et al. |
| 2020/0078180 A1 | 3/2020 | Casey et al. |
| 2020/0085509 A1 | 3/2020 | Roh et al. |
| 2020/0170802 A1 | 6/2020 | Casey et al. |
| 2020/0315708 A1 | 10/2020 | Mosnier et al. |
| 2021/0059822 A1 | 3/2021 | Casey et al. |
| 2021/0210189 A1 | 7/2021 | Casey et al. |
| 2021/0382457 A1 | 12/2021 | Roh et al. |

FOREIGN PATENT DOCUMENTS

| | | |
|---|---|---|
| CN | 204468348 U | 7/2015 |
| CN | 105796214 A | 7/2016 |
| CN | 108670506 A | 10/2018 |
| CN | 110575289 A | 12/2019 |
| CN | 111281613 A | 6/2020 |
| CN | 112155792 A | 1/2021 |
| EP | 3120796 A1 | 1/2017 |
| WO | 2004110309 A2 | 12/2004 |
| WO | 2010151564 A1 | 12/2010 |
| WO | 2014180972 A2 | 11/2014 |
| WO | 2016172694 A1 | 10/2016 |
| WO | 2019112917 A1 | 6/2019 |
| WO | 2019148154 A1 | 8/2019 |

OTHER PUBLICATIONS

International Searching Authority, International Search Report and Written Opinion, PCT Patent Application PCT/US2018/063530, dated Feb. 12, 2019, 16 pages.

Pimenta, Dr. Luiz, "Current Surgical Strategies to Restore Proper Sagittal Alignment," Journal of Spine 2015, vol. 4, Issue 4, 2 pages.

International Search Report and Written Opinion for International Application No. PCT/US19/50885, dated Jan. 28, 2020 (21 pages).

International Search Report and Written Opinion for International Application No. PCT/US19/63855, dated Feb. 14, 2020 (15 pages).

U.S. Appl. No. 15/958,409 for Ryan, filed Apr. 21, 2017.

Extended European Search Report for European Application No. 18885367.5, dated Aug. 16, 2021, 8 pages.

International Search Report and Written Opinion for International Application No. PCT/US21/44878, dated Nov. 16, 2021 (18 pages).

International Search Report and Written Opinion for International Patent Application No. PCT/US21/12065, dated Apr. 29, 2021 (19 pages).

Majdouline et al., "Preoperative assessment and evaluation of instrumentation strategies for the treatment of adolescent idiopathic scoliosis: computer simulation and optimization." Scoliosis 7, 21 (2012), pp. 1-8.

* cited by examiner

SYSTEMS AND METHODS FOR ORTHOPEDIC IMPLANT FIXATION

INCORPORATION BY REFERENCE TO ANY PRIORITY APPLICATIONS

This application claims the benefit of priority to U.S. Provisional Patent Application No. 62/643,046, filed on Mar. 14, 2018, which is herein incorporated by reference in its entirety for all purposes. Priority is claimed pursuant to 35 U.S.C. § 119.

FIELD OF THE INVENTION

The field of the invention generally relates to orthopedic implants, including spinal implants, and methods for designing and producing them.

BACKGROUND

Orthopedic implants are used to correct a variety of different maladies. Orthopedic surgery utilizing orthopedic implants may include one of a number of specialties, including: hand surgery, shoulder and elbow surgery, total joint reconstruction (arthroplasty), skull reconstruction, pediatric orthopedics, foot and ankle surgery, spine surgery, musculoskeletal oncology, surgical sports medicine, and orthopedic trauma. Spine surgery may encompass one or more of the cervical, thoracic, lumbar spine, or the sacrum, and may treat a deformity or degeneration of the spine, or related back pain, leg pain, or other body pain. Irregular spinal curvature may include scoliosis, lordosis, or kyphosis (hyper or hypo), and irregular spinal displacement may include spondylolisthesis. Other spinal disorders include osteoarthritis, lumbar degenerative disc disease or cervical degenerative disc disease, lumbar spinal stenosis or cervical spinal stenosis.

Spinal fusion surgery may be performed to set and hold purposeful changes imparted on the spine. Spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion).

One goal of interbody fusion is to grow bone between vertebra in order to seize (e.g., lock) the spatial relationships in a position that provides enough room for neural elements, including exiting nerve roots. An interbody implant (interbody device, interbody implant, interbody cage, fusion cage, or spine cage) is a prosthesis used in spinal fusion procedures to maintain relative position of vertebra and establish appropriate foraminal height and decompression of exiting nerves. Each patient may have individual or unique disease characteristics, but most implant solutions include implants (e.g. interbody implants) having standard sizes or shapes (stock implants).

SUMMARY OF THE INVENTION

In an embodiment of the present disclosure, an interbody implant system for use in the spine includes a base having two or more bone contacting surfaces, at least one recess in at least one of the two or more bone contacting surfaces, the recess configured for containing a tooth, a deployable tooth to provide fixation between the base and the anatomy of a subject, a break-away bridge between the tooth and the base for providing a first relative position between the tooth and the base, and a locking mechanism for providing a second relative position between the tooth and the base.

In another embodiment of the present disclosure, a method for implanting an implant within the spine of a subject includes providing an interbody implant system for use in the spine includes a base having two or more bone contacting surfaces, at least one recess in at least one of the two or more bone contacting surfaces, the recess configured for containing a tooth, a deployable tooth to provide fixation between the base and the anatomy of a subject, a break-away bridge between the tooth and the base for providing a first relative position between the tooth and the base, and a locking mechanism for providing a second relative position between the tooth and the base, inserting the interbody implant between two vertebrae of the spine of the subject with the tooth and the base in the first relative position, and moving the tooth and the base into the second relative position.

DETAILED DESCRIPTION

An interbody implant and an efficient method of producing the patient-specific implant are described in the embodiments herein. Implants according to embodiments described herein may include interbody implants or fusion cages. The interbody implants are typically intended to be placed between two vertebral bodies. Oftentimes, the intervertebral disc is removed prior to the placement of the interbody implant. The lower side of an interbody implant is intended to abut at least a portion of an upper side (endplate) of a first vertebral body and the upper side of the interbody implant is intended to abut at least a portion of a lower side (endplate) of a second vertebral body.

Insufficient contact and load transfer between the vertebral body and the interbody implant can produce inadequate fixation and can allow the cage to move relative to the vertebral body. Furthermore, insufficient contact area or fixation between the interbody implant and the vertebral bodies can result in micro-motions and/or macro-motions that can reduce the opportunity for bone growth and fusion to occur. If enough motion occurs, expulsion of the interbody implant can result.

Presently, fixation elements (including teeth, barbs, or screws) can be used to provide fixation of the interbody implant to the adjacent vertebral bodies. These fixation elements can be static features, such as teeth, on the opposing surfaces of the interbody that are designed to contact the vertebral endplates. Additionally, screws or barbs can be delivered following delivery and placement of the interbody implant. In these cases, these screws and barbs are driven through openings in the interbody implant and into the adjacent vertebral bodies. Each of these elements and features are designed to create fixation between the implant and adjacent anatomy.

Low bone mineral density index, overaggressive discectomies, or decortications of the endplate can reduce the strength of the anatomic endplate and reduce the ability to provide sufficient fixation to the interbody implant and reduce the transfer load from one vertebral body to another. To reduce or eliminate these risks, surgeons carefully prepare the opposing vertebral endplates. The surgeon aims to insert an interbody implant having as large a footprint (coverage area) as possible, in order to maximize the contact surface between implant and anatomy. When appropriate, the surgeon also places the interbody implant on the apophyseal rings to provide as much support and load transfer as possible for spinal distraction. The surgeon must also ensure the interbody implant is securely positioned within the disc space.

Figure 1:
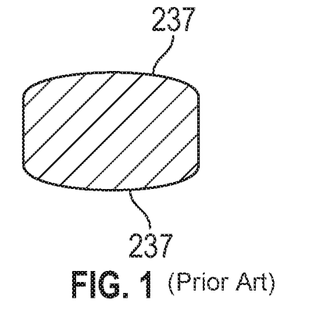
FIGS. 1-22 illustrate a variety of implants configured as intervertebral bodies and spacers, bone plates, pins, dowels, and the like, according to embodiments of the present disclosure.
Figure 2:
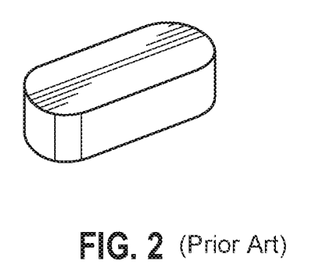
Figure 3:
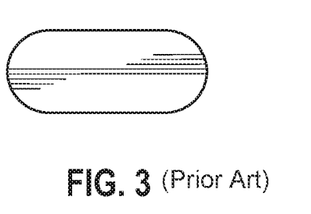
Figure 4:
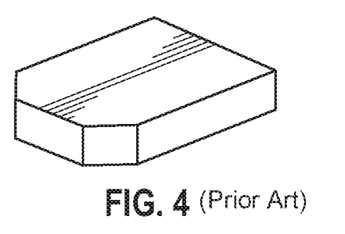
Figure 5:
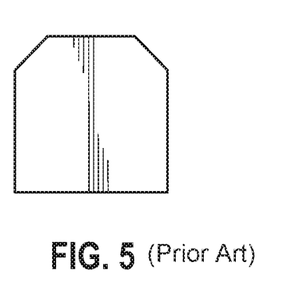
Figure 6:
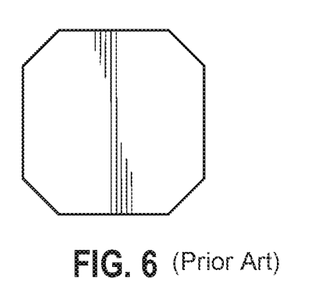
Figure 7:
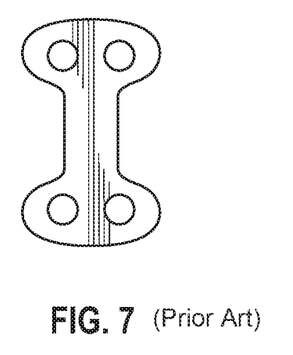
Figure 8:
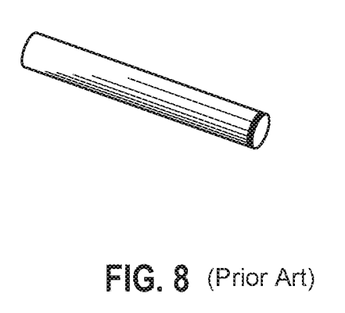
Figure 9:
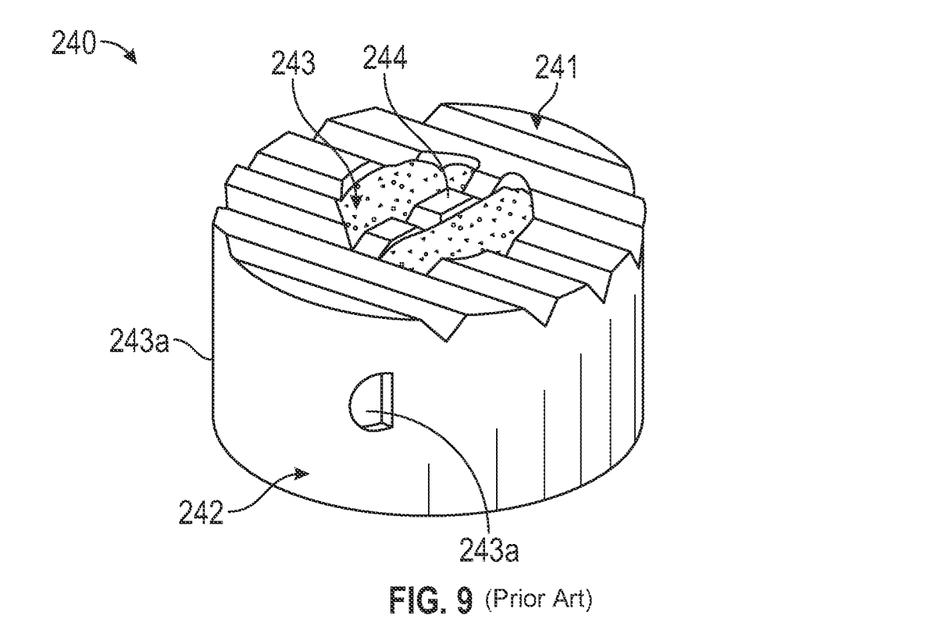
Figure 10:
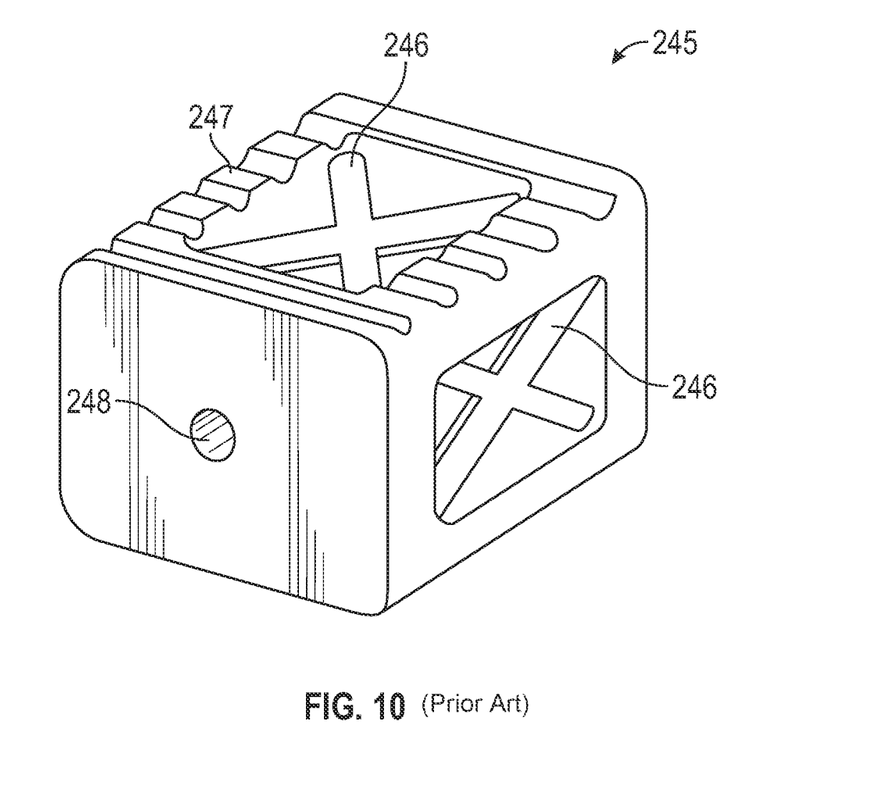
Figure 11:
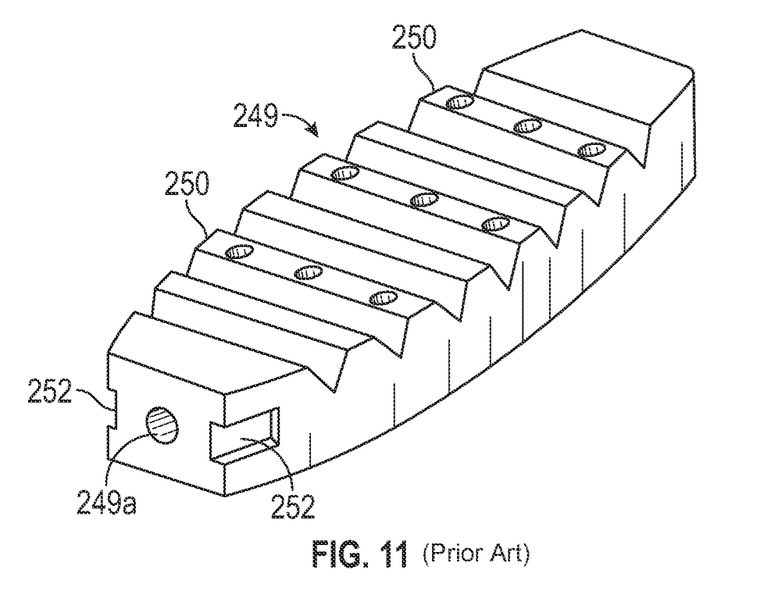

FIGS. 1-22 illustrate a variety of implants which may be produced by the systems and methods described herein, according to several embodiments of the present disclosure. FIG. 1 illustrates an intervertebral implant possessing biconvex surfaces 237 which are configured to match the curvatures of the vertebral endplates with which they come into contact. The biconvex surfaces 237 may each curve laterally (left to right), or curve anteriorly-posteriorly, or curve both laterally and anteriorly-posteriorly (e.g., a hemisphere or other three-dimensional convex shape). FIGS. 2-6 show various views of implants that are suitable for interbody use, including the oval footprints of FIGS. 2-3, the hexagonal footprints of FIGS. 4-5, or the octagonal footprint of FIG. 6. In some embodiments, other polygonal footprints may be utilized. In some embodiments, the footprint may comprise sides that are equal in length to each other, or in other embodiments, none of the sides may be equal in length to each other. FIG. 7 shows a cervical bone plate for the fixation of adjacent cervical vertebrae. The bone plate spans two or more vertebrae, but does not necessarily fill the space between two vertebral endplates. The size and shape of the bone plate of FIG. 7, including the location of the holes for screws, may be configured to maintain the cervical vertebrae in a particular relation to each other. FIG. 8 illustrates a cylindrical pin or dowel which may be keyed (not shown) to facilitate its installation. FIG. 9 illustrates an intervertebral implant 240 having a textured surface 241, e.g., roughenings, knurlings, ridges, and the like, to resist backing-out of the implant following its insertion in the intervertebral space. Surfaces 241 may converge to provide an anterior ramp configuration possessing a suitable lordotic angle or the surfaces may be essentially flat. The outer profile 242 of the implant can be round, oval, square, diamond-shaped, octagonal, hexagonal, etc., as requirements suggest. The implant can be provided with an opening 243 for receiving a quantity of osteogenic/osteoinductive material and/or a rigid reinforcing member 244 for added strength. The walls of the implant possess a pair of inserter instrument interfaces 243a (only one shown) for engagement with one end of an insertion tool. FIG. 10 depicts an open, or cage-like, structure 245 suitable for use as an anterior or posterior intervertebral implant. Cross braces 246 on one or more sides of the implant provide increased structural strength over that of a totally open configuration. The open space can be advantageously filled with an osteogenic/osteoinducting material. Texturized surfaces, e.g., ridges 247 are provided to resist backing-out of the implant following its installation. Inserter interface 248 is intended to receive the distal (working end) of an implant insertion tool. FIG. 11 illustrates an intervertebral implant 249 possessing a position-retaining textured surface 250 (ridges) and a pattern of orifices communicating with the interior which possesses a void structure. The sides of the implant at one end thereof have a matching pair of implant inserter interfaces 252 which are intended to be grasped by an insertion tool. One end of the implant possesses an orifice 249a through which an osteogenic/osteoinductive material can be introduced into the interior void communicating channels of the implant.

Figure 12:
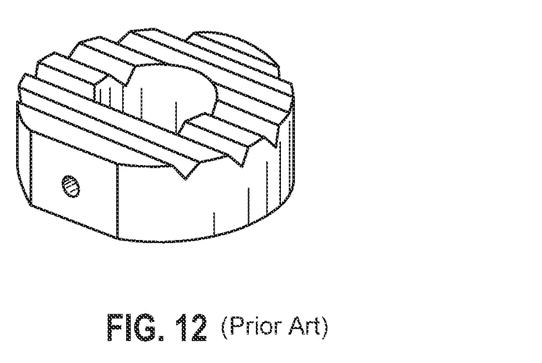
Figure 13:
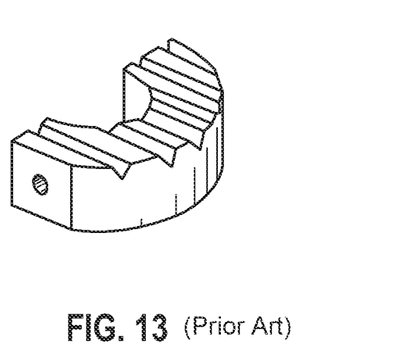
Figure 14:
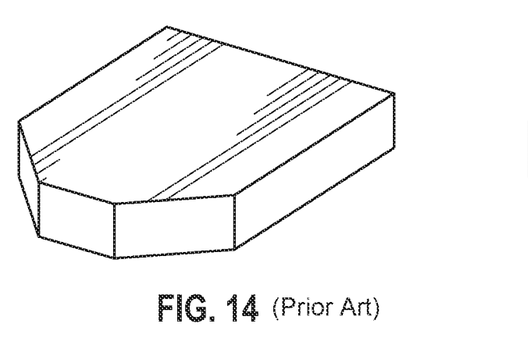
Figure 15:
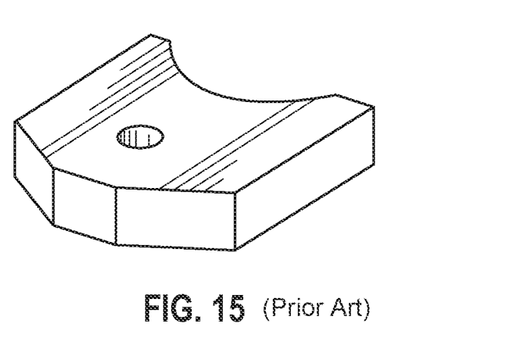
Figure 16:
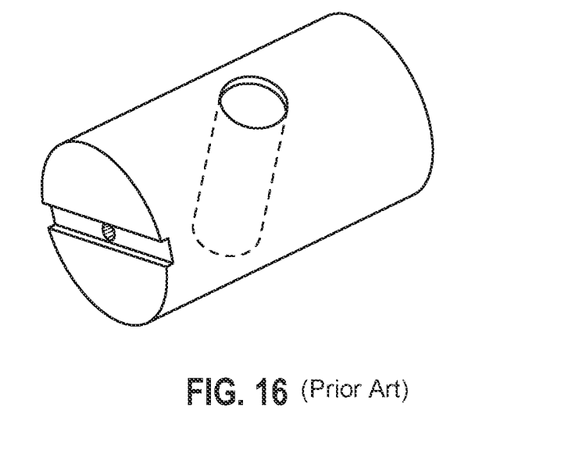
Figure 17:
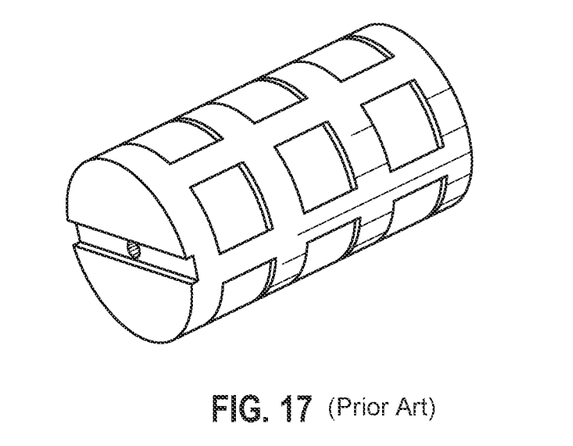
Figure 18:
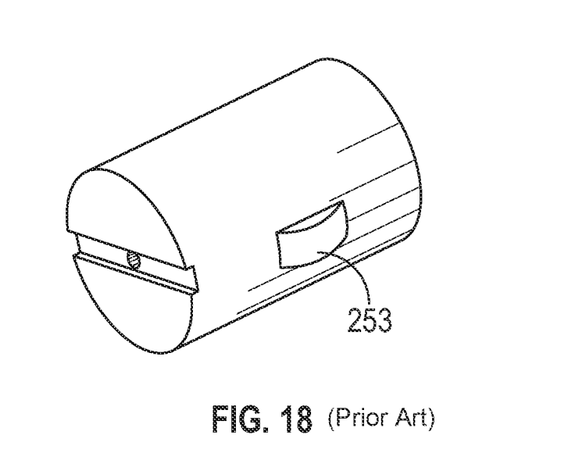
Figure 19:
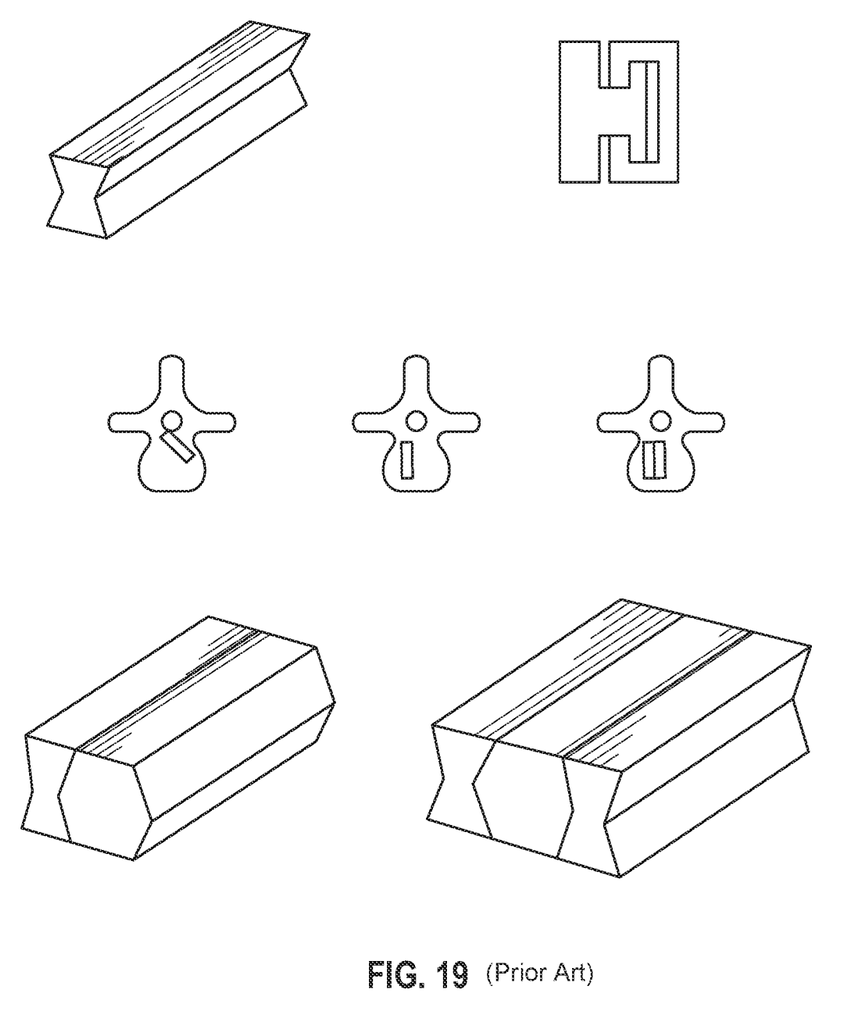
Figure 20:
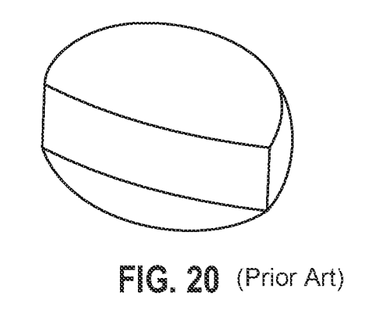
Figure 21:
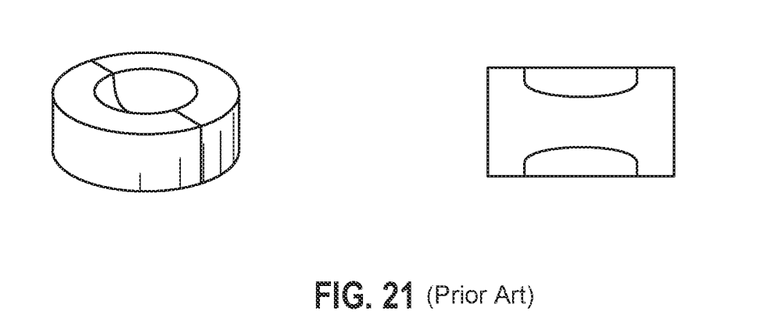
Figure 22:
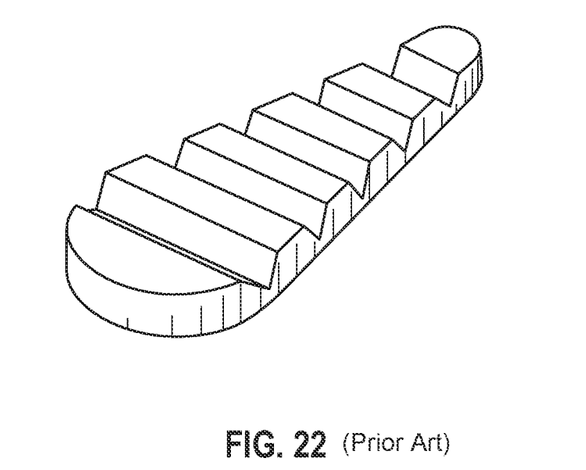

FIGS. 12-15 show various additional configurations of implants for insertion in the intervertebral space: FIG. 12 (an anterior ramp implant), FIG. 13 (a posterior ramp implant), FIG. 14 (a cervical spacer) and FIG. 15 (a cervical spacer including a radiused recess at one side). FIGS. 16-18 show various implants configured as intervertebral dowels. The implant of FIG. 16 is a solid structure with a through bore for receiving osteogenic/osteoinductive material. The implant of FIG. 17 possesses an open, or cage-like, structure which can be packed with osteogenic/osteoinductive material. The implant of FIG. 18 possesses at least one wing-like structure 253 on its longitudinal surface which prevents rotational displacement within the intervertebral space. Each of implants 16-18 possesses a slot and hole for receiving the distal end of an insertion tool. FIG. 19 illustrates a transforaminal lumbar interbody fusion (TLIF) implant and its assembly from subunits. The implant of FIG. 19 may alternatively be used as a posterior lumbar interbody fusion (PLIF) implant. FIG. 20 depicts a convex anterior interbody ramp with openings communicating with the interior. FIG. 21 shows another embodiment of anterior interbody implant. FIG. 22 shows a solid anterior interbody implant presenting a large surface area for implant-vertebral endplate contact.

Figure 23:
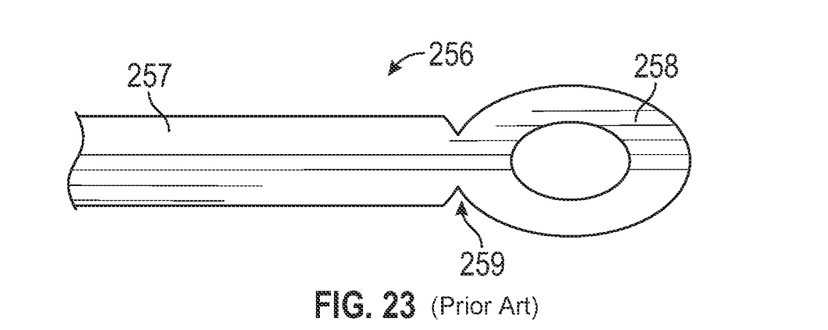
FIG. 23 illustrates the distal end of an integral implant insertion instrument and implant, according to an embodiment of the present disclosure.

FIG. 23 schematically illustrates in plan view the distal end 257 of an integral, or combined, implant insertion instrument and implant 256 wherein implant portion 258 specifically, an intervertebral implant, is joined to the distal end 257 of the instrument portion through a weakened, or break-away, site of attachment 259. Following insertion of the intervertebral implant in the intervertebral space, application of a sharp upward or downward movement of the implant insertion instrument will result in the distal end of the instrument cleanly breaking away, and separating from, the implant which remains in place. Alternatively, the site of attachment 259 may comprise any mechanism that allows the distal end 257 to releasably grip or maintain the implant 258, including, but not limited to: a clamp, an adhesive, epoxy, or hot melt attachment, a magnetic connection, a snap, a threaded attachment, a tapered attachment, a spring attachment, and a combination of any two or more of these attachment features. Custom instruments may even be produced by the systems and methods described herein. For example, a particular patient may have a deformity which requires an instrument having a particular angle that is not available in off-the-shelf instruments.

Figure 24:
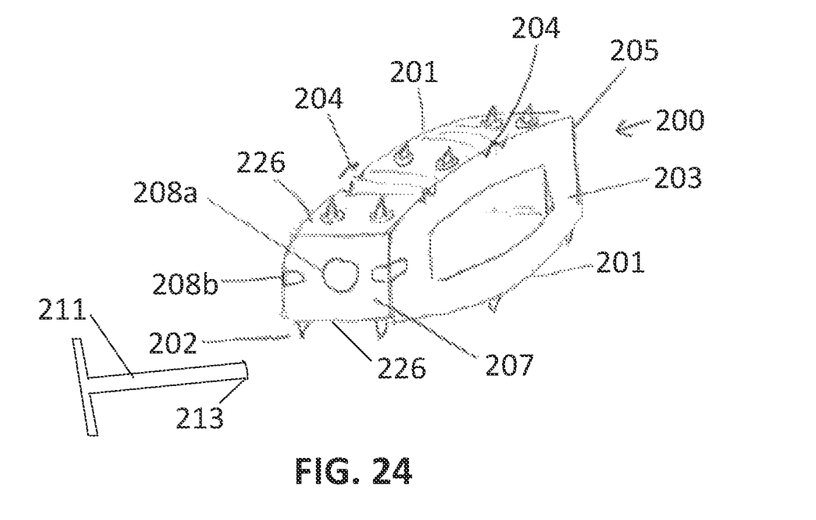
FIG. 24 shows an interbody implant having deployable teeth.

FIG. 24 shows an interbody implant 200 having opposing bone contacting surfaces 201, opposing lateral surfaces 203, an anterior surface 205, and a posterior surface 207. Surfaces 201, 203, 205, 207 form a three-dimensional implant 200. Surfaces 201, 203, 205, 207 can be planar or curved. When curved, the surfaces 201, 203, 205, 207 may each comprise a concave surface or a convex surface. In some embodiments, the surfaces 201, 203, 205, 207 can become contiguous and uninterrupted. In some cases, the cross section can be circular, semi-circular, U-shaped, or C-shaped.

In one embodiment, implant 200 contains static fixation features 204, and dynamic fixation features 202 extending from a base portion 226 of the implant 200. Static teeth 204 are configured to provide temporary fixation between the interbody implant 200 and a first adjacent vertebral body. Dynamic teeth 202 are deployed after delivery of the implant 200 to a desired location within the intervertebral space, and configured to provide fixation to a second adjacent vertebral body. During implantation, implant 200 is inserted into the intervertebral space and adjusted to the location using insertion and adjustment tools. The tools can be designed to mate with features 208a, 208b on the interbody implant 200. Features 208a, 208b may comprise indentations, grooves, ribs, bumps, or other geometric designs to which tools may be engaged.

Figure 25:
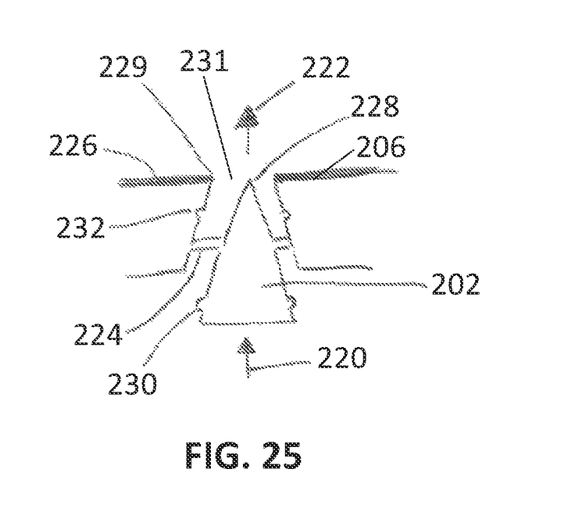
FIG. 25 shows a cross section of the interbody implant at the location of a deployable tooth. In this figure, the tooth is in the un-deployed state.

FIG. 25 shows a cross section of a dynamic tooth 202 in a first position relative to opening 231 (undeployed). In one embodiment, tooth 202 is positioned sub-flush relative the surface of implant 200. Additive manufacturing processes are utilized which enable fabrication of features 230, 232, teeth 202, bridges 224 to create a mechanism that can be optimized to provide dynamic teeth 202. Additive manufacturing processes may include one or more of: three-dimensional printing, vat polymerization, stereolithography (SLA), selective laser melting (SLM), powder bed printing (PP), powder bed fusion, sheet laminarization, material extrusion, selective laser sintering (SLS), selective heat sintering (SHM), fused deposition modeling (FDM), direct metal laser sintering (DMLS), laminated object manufacturing (LOM), laminar deposition, thermoplastic printing, direct material deposition (DMD), digital light processing (DLP), inkjet photo resin machining, and electron beam melting (EBM). These features 230, 232, teeth 202, bridges 224 can be difficult to create and optimize using traditional manufacturing methods (milling, turning, etc.). Additive manufacturing, building parts layer-by-layer, can be used to create features 230, 232, teeth 202, bridges 224 of a mechanism that can be optimized to create, first, a break-away (separation of tooth 202 from the base portion 226 of the implant 200) and, after break-away, a seized relationship between the base portion 226 of the implant 200 and the tooth 202. Another advantage of employing additive manufacturing is the ability to create patient-specific implants that are designed to optimally fit each patient. The implant 200 may include any of the embodiments described herein, or may include embodiments of implants or may incorporate the methods for designing and making implants, such as those disclosed in co-pending U.S. patent application Ser. No. 16/207,116, filed on Dec. 1, 2018, and entitled "Systems and Methods for Multi-Planar Orthopedic Alignment," which is incorporated by reference herein in its entirety for all purposes.

For example, some embodiments utilize a system for producing patient-specific implants. In some embodiments, scan data is obtained from a CT scan of a patient, for example, a CT scan that includes the spine of the patient, or at least the portion of interest in the spine. In other embodiments the scan data may comprise MRI scan data or x-ray data. The CT scan data is converted into a three-dimensional image through software manipulation of the data. Typically, CT scan data is presented in a DICOM format, which includes individual slices of imaging data. A common slide thickness is one mm, though other thickness may be used, such as 0.25 mm, 0.5 mm, 1.5 mm, 2.0 mm, 2.5 mm, 3.0 mm and greater thicknesses. Spine segments may be selected for analysis. For example, a user interface that is associated with at least one computer memory that is not a transitory signal and which comprises instructions executable by at least one processor may be utilized to select a region of interest. In some cases, the region of interest may be a diseased or deformed portion of the spine, including a particular number of successive vertebrae and their surrounding soft tissue. In some cases, the entire spine may be selected. In some cases, only sacral and lumbar vertebrae and their surrounding soft tissue are selected. In some cases, only lumbar and thoracic vertebrae and their surrounding soft tissue are selected. In some cases, only cervical vertebrae and their surrounding soft tissue are selected.

The system may contain a memory and a processor, and may include any number of custom stand-alone devices, or any mobile device, such as an iPhone, smart phone, iPAD, smart watch, laptop or desktop computer. The system may also include a user interface. The system may also be configured to access the memory remotely, for example, via internet browser access or other wireless means. The three-dimensional image can be converted into a form such that it can be manipulated by a user to measure anatomical deformities related to the disease (e.g., spine disease). The information can then be used by a medical professional, or technical or engineering professional in conjunction or collaboration with a medical professional, to design the optimized geometry of the corrected spine, thus allowing the design of an implant to treat the particular disease or malady.

In one embodiment, the teeth 202 can be temporarily affixed to the base portion 226 of the implant body 200 (e.g., via the bridges 224 which extend between each tooth 224 and the base portion 206 of the implant 200). During insertion of the implant 200 into the desired location within the intervertebral space, the tip 228 of each tooth 202 is positioned within recess 229 and opening 231 at or near the surface 206 of the implant 200. In one embodiment, tips 228 of teeth 202 are positioned below the surface 206 of implant 200 (sub-flush). In this embodiment, tips 228 are protected and are not subjected to loads during insertion and positioning of the implant 200. Furthermore, tips 228 can be made sharp and can remain sharp in order to penetrate adjacent anatomy and provide fixation.

Following placement of implant 200 in the desired location, a tool 211 can be used to deploy teeth 202 to a position that is super-flush relative to the surface 206. For example, the tool 211 may have a tip 213 configured to insert into feature 208a to apply a force to cause both separation of the tooth 202 from the base portion 206 of the implant 200, and to cause the tooth 202 to be extended from its flush or sub-flush position (e.g., the first, undeployed position). In some embodiments, an axial force 220 can be delivered to tooth 202 with the tool 221. In some embodiments, the tool 221 may be configured to apply a torque, as does a screwdriver, that in turn places an axial force 220 on the tooth 202. In some embodiments, the tool 221 may be configured to apply a force along an axis extending between two surfaces (e.g., along an axis extending between the anterior surface 205 and the posterior surface 207) in order to release a spring element or other element that transversely applies an axial force 220 on the tooth 202. In use, the axial force 220 causes the tooth 202 to move in an axial direction 222 to extend from the surface 206 and penetrate the adjacent vertebral endplate. In one embodiment, tooth 202 may be connected to implant 200 with a break-away bridge 224 or a series of break-away bridges 224. Axial force 220 can fracture bridge 224 and allow axial translation 222 of tooth 202. Locking features 230, 232 can be positioned on tooth 202 and implant 200 to provide fixation between implant 200 and tooth 202. Locking features 230, 232 may comprise protrusions 230 and indentations 232, configured to fit into each other. In some embodiments, the protrusions 230 may be configured to permanently snap permanently into the indentations 232. In some embodiments, the protrusions 230 may be configured to removably fit into the indentations 232. The protrusions 230, when snapped into the indentations 232 may have a minimum unsnapping force of at least about 50 pounds. In some embodiments, the protrusions 230 and indentations 232 may each have lead-ins (e.g. tapers) that each the snapping of the protrusion 230 into the indentation 232, but not have lead-ins on the opposite sides of the protrusions 230 and indentations 232, such that unsnapping is not possible, or is at least very difficult or requires an unlikely high force to achieve.

Figure 26:
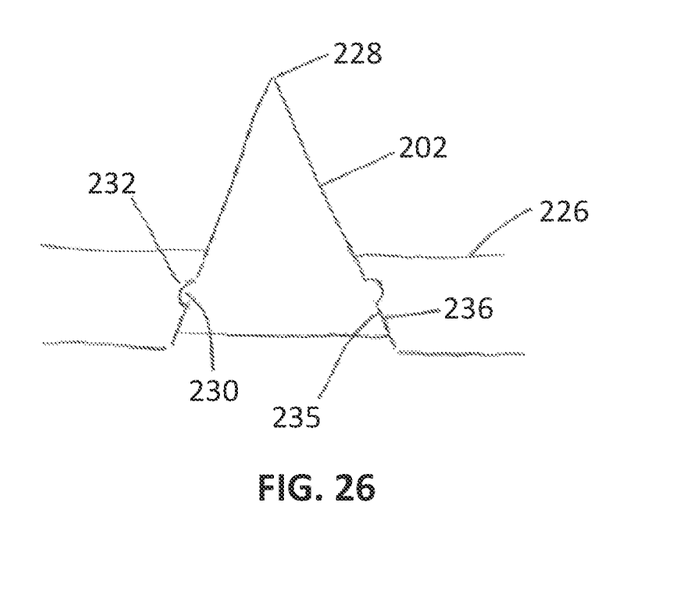
FIG. 26 shows a cross section of the interbody implant at the location of a deployable tooth. In this figure, the tooth is in the deployed state.

FIG. 26 shows a cross section of the tooth 202 in a second position (fully deployed). In one embodiment, tooth 202 is deployed and wedged or engaged into position. The sizing of opening 231 in relation to the tooth 202 is such that the tooth cannot be expulsed from the opening 231. In one embodiment, expulsion of the tooth cannot occur because the opening 231 is smaller than the dimensions at the larger end of tooth 202 (bottom of FIG. 26). Furthermore, the sizing of tooth 202 and opening 231 is such that tooth 202 cannot be permanently disassociated from the implant due to the fit of tooth 202 within opening 231.

The post-deployment relationship between tooth 202 and implant 200 is preserved using interference fits between locking features 230, 232 and/or surfaces 235, 236. In some embodiments, the locking features 230, 232 are absent, and instead, the tooth 202 frictionally engages within the recess 229 (via surfaces 230, 232) at the base portion 226 when the tooth 202 is axially extended. In other embodiments, flash (remaining material) from the broken break-away bridges 224 may provide the slight interference with which the tooth 202 frictionally engages with the recess 229. The features 230, 232 may include bumps, recesses, annual grooves, ridges, rings, incomplete rings, split rings, buttons, springs, or other three-dimensional features to provide secure engagement between tooth 202 and implant 200. Other mechanisms, such as friction, interference, and deformation between surfaces of tooth 202 and opening 231 can seize the relationship between components. In other embodiments, the bridge 224 may comprise a break-away adhesive joint, a break-away tack or weld, or a magnetic coupling. In other embodiments, the bridge 224 may comprise a flexible joint, an over-center mechanism, a linkage, any of which may include a locked condition and an unlocked condition. The locked condition may be the condition when delivered and the unlocked condition may be achieved by the application of a substantially axially-directed force placed upon the tooth 202 or upon the bridge 224 or upon the tooth 202 and the bridge 224. In other embodiments, a non-axially directed force or a moment (e.g., torque) may be applied to the tooth 202 and/or the bridge 224 in order to change the bridge from a locked condition to an unlocked condition.

Interbody 200 can be manufactured of materials typical of medical implants, including, but not limited to, titanium, titanium alloy, Ti6Al4V, polymers, polyether ether ketone (PEEK), etc.

The systems and methods described herein are configured to provide a three-dimensional shape that represents the ideal implant to fit into the negative space of the spine, once the spine receives the appropriate manipulation in the coronal, sagittal, and axial planes. In other words, the custom shape of the implant will at least partially provide and maintain the desired correction to the spine. Thus, the coronal, sagittal, and axial plane deformities of the spine are corrected, allowing restoration of the anatomical function of the spine. The correction may include both rotation and/or linear displacement along the degrees of freedom. For example, positive displacement along the x-axis, negative displacement along the x-axis, positive rotation around the x-axis, negative rotation around the x-axis, positive displacement along the y-axis, negative displacement along the y-axis, positive rotation around the y-axis, negative rotation around the y-axis, positive displacement along the z-axis, negative displacement along the z-axis, positive rotation around the z-axis, negative rotation around the z-axis.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

While embodiments have been shown and described, various modifications may be made without departing from the scope of the inventive concepts disclosed herein.

What is claimed is:

1. A patient-specific interbody implant system for use in a patient's spine, comprising:
   a base comprising two or more bone contacting surfaces including a first bone contacting surface having a first patient-specific shape configured to match a first vertebral endplate and a second bone contacting surface having a second patient-specific shape configured to match a second vertebral endplate of the patient, wherein the first patient-specific shape and the second patient-specific shape are non-invasively determined from a user-adjustable virtual three-dimensional model of at least the first vertebral endplate and the second vertebral endplate, the first patient-specific shape and the second patient-specific shape based on a version of the user-adjustable virtual three-dimensional model that incorporates one or more virtual user manipulations of the user-adjustable virtual three-dimensional model;
   at least one recess in at least one of the first or second bone contacting surfaces, the recess configured for containing a tooth;
   a deployable tooth configured to provide fixation between the base and at least one of the first or second vertebral endplates;
   a break-away bridge between the tooth and the base for providing a first relative position between the tooth and the base; and
   a locking mechanism for providing a second relative position between the tooth and the base,
   wherein the patient-specific interbody system is configured to provide a patient-specific correction to the patient's spine corresponding to the version of the user-adjustable virtual three-dimensional model that incorporates the one or more virtual user manipulations when the patient-specific interbody system is implanted between the first vertebral endplate and the second vertebral endplate.

2. The system of claim 1, further comprising an opening that is configured to allow displacement and restrict expulsion of the deployable tooth from one recess of the at least one recess.

3. The system of claim 1, further comprising an opening in one recess of the at least one recess sized such that the tooth cannot be permanently disassociated from the implant.

4. The system of claim 1, wherein the first relative position is sub-flush and the second relative position is super-flush.

5. The system of claim 1, wherein the tooth comprises a sharp tip to provide fixation between the base and the anatomy of the subject.

6. The system of claim 1, wherein the break-away bridge is configured to fracture when the tooth is subjected to a substantially axially-directed force.

7. The system of claim 1, further comprising one or more additional teeth and one or more additional recesses configured to correspond with the one or more additional teeth.

8. The system of claim 1, wherein the locking mechanism comprises friction between the tooth and the base.

9. The system of claim 1, wherein the locking mechanism comprises an interference fit between the tooth and the base.

10. The system of claim 1, wherein the locking mechanism comprises inter-locking features between the tooth and the base.

11. The system of claim 1, wherein the implant comprises at least one of Titanium, Ti6A14V, or Titanium alloy.

12. The system of claim 1, wherein the implant comprises a polymer.

13. The system of claim 1, wherein the implant comprises polyether ether ketone (PEEK).

14. A system of claim 1, wherein the implant comprises one or more additive manufactured features.

15. The system of claim 1, wherein the two or more bone contacting surfaces comprise two opposing bone contact surfaces.

16. The system of claim 1, wherein the break-away bridge comprises a first, locked condition, and a second, unlocked condition, the second unlocked condition activated by the application of a force or moment.

17. A method for implanting a patient-specific implant within a spine of a patient, comprising:
   non-invasively determining a patient-specific correction for the spine of the patient by adjusting a virtual three-dimensional model of at least a portion of the spine of the patient;
   providing a patient-specific interbody implant based at least in part of the adjusted virtual three-dimensional model and configured to provide the patient-specific correction when implanted in the spine of the patient, the patient-specific implant comprising:
      a base comprising two or more bone contacting surfaces including a first bone contacting surface having a first patient-specific shape configured to match a first vertebral endplate and a second bone contacting surface having a second patient-specific shape configured to match a second vertebral endplate of the patient;
      at least one recess in at least one of the first or second bone contacting surfaces, the recess configured for containing a tooth;
      a deployable tooth configured to provide fixation between the base and at least one of the first or second vertebral endplates;
      a break-away bridge between the tooth and the base for providing a first relative position between the tooth and the base; and
      a locking mechanism for providing a second relative position between the tooth and the base;
   inserting the patient-specific interbody implant between the first and second vertebral endplates of the patient with the tooth and the base in the first relative position; and
   moving the tooth and the base into the second relative position.

* * * * *